United States Patent [19]

Hoffman

[11] Patent Number: 4,480,994
[45] Date of Patent: Nov. 6, 1984

[54] ORTHODONTIC OCCLUSION PREVENTION SYSTEM

[76] Inventor: Carl S. Hoffman, 390 Crestwood Dr., Cheshire, Conn. 06410

[21] Appl. No.: 489,871

[22] Filed: Apr. 29, 1983

[51] Int. Cl.³ .............................................. A61C 7/00
[52] U.S. Cl. ...................................................... 433/6
[58] Field of Search ........................................ 433/6, 7

[56] References Cited

U.S. PATENT DOCUMENTS 3,478,429 11/1969 Shilliday ................................ 433/6
3,724,075 4/1973 Kesling .................................. 433/6
4,392,826 7/1983 Goshgzrian ........................... 433/7

Primary Examiner—Robert Peshock
Attorney, Agent, or Firm—Paul J. Sutton

[57] ABSTRACT

An inter-incisal non-voluntary orthodontic device intended for use in conjunction with overbite corrective braces. The device includes plate of thermoplastic material positioned over selected upper anterior teeth that acts to prevent contact between the selected upper anterior teeth and the opposing lower anterior teeth. The plate by preventing contact between the anterior upper and lower teeth also prevents occlusion between the upper and lower posterior teeth. The plate is anchored to selected upper molars in such a way that the patient cannot easily remove the plate. The plate is connected to selected upper molars, preferably the first molars at sheaths connected to molar jackets used to anchor the patient's braces. Additional anchoring is provided by a ligature through an aperature in the front of the plate and under the brace wire.

9 Claims, 8 Drawing Figures

ORTHODONTIC OCCLUSION PREVENTION SYSTEM

BACKGROUND OF THE INVENTION

The present invention relates generally to orthodontic mechanical devices that aid in the treatment of vertical dental overbite, and in particular to orthodontic devices that aid in constraining patients to modify their diets while overbite appliances are in place.

Certain obstacles generally arise during the treatment of patients having vertical dental overbite. One of these problems is a lack of voluntary modification of diet by the patient while the orthodontic device meant to correct the overbite is being worn by the patient. In particular, it may be said that certain teenagers are less responsive to outside suggestion or discipline than others. The reasons for this is not an area for discussion here, but many of those in the dental field, in particular in the field of orthodontics, would probably agree that many young patients are motivated not to comply with the dentist's instructions and often refuse to cooperate voluntarily. This brings up the necessity of resorting to "non-voluntary" devices that cannot be removed by the patient, or at least cannot be removed and then replaced without detection by the treating dentist.

One particular need then in the field of orthodontists is to provide a non-voluntary device that can be selectively used for certain non-cooperative type young patient's teeth but also cannot be easily removed by the patient. For any such device certain criteria must be met. Some of these criteria are as follows:

1. Lack of interference with tooth movement of a primary multiband appliance so as to avoid the need for consecutive stages of treatment as opposed to more rapid and direct simultaneous mechanical actions.
2. Machine mass production to reduce costs of fabricating individualized appliance in the laboratory. That is, impressions would not be necessary.
3. Total elimination of horizontal obstruction to mandibular repositioning.
4. Barrier to mastication of non-recommended diet components.
5. Maximized freedom of eruption of posterior teeth to assist in leveling.
6. Complete lack of patient control of appliance.
7. Absolute indication of patient interference.
8. Rapid effect to allow shortest period of use.
9. Minimal obstruction to oral hygiene.
10. Ability to be readily modified as tooth movement occurs.
11. Lack of gingiual contact.

It is to be noted that the device needed is not generally to be used alone but is generally to be applied in conjunction with other orthodontic devices already in place on the teeth that act to correct the problem of dental overbite and in particular aim at correcting the posture of the mandible.

The present invention contemplates a novel, non-voluntary orthodontic appliance that meets the need described above and in addition meets the criteria listed.

Accordingly, it is an object of my invention to provide an inter-incisal orthodontic plate that opens the posterior occlusion and prevents the contact of the upper anterior teeth with the lower anterior teeth.

It is a further object of my invention to provide an orthodontic inter-incisal plate having an anterior bite plate that is in contact with the incisal edges of the upper anterior teeth.

It is a further object of my invention to provide an inter-incisal plate that has a pair of support wires extending from either side of the plate to upper first molar lingual sheaths connected to the dental brackets without interfering with the bicuspid or cuspid teeth.

It is a further object of this invention to provide an inter-incisal plate that is connected to first molar lingual sheaths by means of a pair of anchoring wires connected to the plate, the wires having step-down bends and being disposed along the dental arch so as to avoid contact with the cuspid and bicuspid teeth.

It is a further object of the present invention to provide an inter-incisal plate having a pair of support wires for mounting to the lingual sheaths of the upper first molars that have excess wire for length and width adjustment.

It is a further object of the present invention to provide an inter-incisal plate having wire for connecting the plate to the first molars that has a folded back portion of wire forming a double strand that is adapted to be fit in first molar sheaths and that the double strand portion extends 3 to 4 millimeters in a posterior direction beyond the distal end of the first molars and bends inwardly to form a stop against the support wires from sliding anteriorly in the sheath.

It is a further object of this invention to provide an inter-incisal plate anchored by support wires to lingual sheaths of the first molars, the support wires forming a pair of double strand portions that have a single strand end positioned in proximity to the sheaths anteriorly of the sheaths, the single strand on each being bent upwards to provide a stud stop against posterior movement of the wires in the sheaths.

It is a further object of this invention to provide an inter-incisal plate that is positioned in contact with the upper anterior teeth and is in part anchored by a ligature through an aperture in the plate to the brace wire.

It is yet a further object of my invention to provide an inter-incisal plate that separates the upper and lower anterior teeth and in so doing, separates the upper and lower posterior teeth so as to prevent the patient from masticating certain foods.

It is yet another object of this invention to provide an inter-incisal plate that prevents mastication of certain foods and in addition cannot be easily removed by the patient.

It is yet another object of my invention to provide a non-removable inter-incisal plate that does not interfere with the tooth movement directed by primary multiband appliances.

It is yet a further object of this invention to provide an inter-incisal plate that is inexpensive to produce and that can be fitted to a patient's upper anterior teeth without the necessity of fabricating an individual appliance in the office or laboratory, that is, without having to make an impression.

It is another object of my invention to provide an inter-incisal plate that totally eliminates horizontal obstruction to mandibular repositioning.

It is yet another object of this invention to provide an inter-incisal plate that maximizes feedom of eruption of posterior teeth to assist in leveling.

It is still another object of my invention to provide an inter-incisal plate that is wired to the patient's posterior upper teeth in such a manner that once removed by the patient is difficult to remount by the patient.

It is a further object of this invention to provide a non-voluntary inter-incisal plate that creates a minimal obstruction to oral hygiene.

It is another object of my invention to provide a non-voluntary inter-incisal plate that can be readily modified by the orthodontist as tooth movement occurs.

It is yet a further object of this invention to provide a non-voluntary inter-incisal plate that is free of gingival contact.

The present invention fulfills the above objects and overcomes limitations and disadvantages of prior art solutions to problems by providing a novel device that is positioned against the upper anterior teeth that comprises a plate mounted against selected upper anterior teeth that comprises a plate mounted against selected upper anterior teeth adapted to prevent contact between the upper anterior teeth and the opposed lower anterior teeth and a wire that is connected to the plate and to selected upper posterior teeth so that the plate is anchored to the selected upper posterior teeth. The plate thus prevents occlusion between the upper and lower posterior teeth. The selected upper anterior teeth are preferably lateral and central incisors. The preferred selected upper posterior teeth are the first molars. The plate preferably is a substantially flat plate having opposed, substantially parallel top and bottom walls intersected by a vertical rear wall and a C-shaped front wall configured in accordance with the upper anterior incisors. The rear wall extends substantially at right angles to the mesial, or midline, of the mouth. The wire includes a pair of strands each having one end connected to the rear wall of the plate and the other end being folded back into a double strand portion. The double strand portion includes a folded distal end and a strand end positioned between the folded distal end and the plate. Jackets are mounted around the upper first molars and sheaths are connected to the lingual side, or inner, walls of the jackets. Each double strand portion is slidably mounted to the sheaths. The sheaths are disposed between the folded distal ends and the strand ends. The folded distal ends are bent inwardly and the strand ends are bent upwardly, so that the distal ends and the strand ends form stops adapted to prevent the double strand portions from sliding in the sheaths. The plate is additionally anchored in position by means of a ligature tied through on aperture in the plate that is positioned over the center line of the upper central incisors. The ligature is passed over the brace wire on the upper teeth and tied. The plate is preferably of thermoplastic material.

An alternate embodiment includes a pair of support wires of heavy metal that is imbedded into a pair of posts disposed on the top wall of the plate. The wires extend to the sheaths of the first molars where they are connected. Each wire includes an anterior stop bend and a posterior bend that prevent the wires from sliding in the sheaths.

The invention will be more clearly understood from the following description of a specific embodiment of the invention together with the accompanying drawings, wherein similar reference characters denote similar elements throughout the several views, and in which.

It is noted here that I have a prior invention "Orthopedic Pressure Appliance and Method for Controlling Development of the Maxillary Bone," U.S. Pat. No. 4,337,036, that is an orthopedic pressure appliance adapted to be retained in the mouth with resilient wires attached to a headcap that has certain superficial features to the present invention. The terminology used therein will differ slightly in some respects from that used herein. It is understood that the terminology of each invention will stand alone and not be referred one to the other.

Reference is now made in detail to the drawings. In the detailed description that follows the terms "left" and "right" refer to the side of the jaw as would be referred to by the patient and not as would be referred to from the vantage of an observer.

Figure 1:
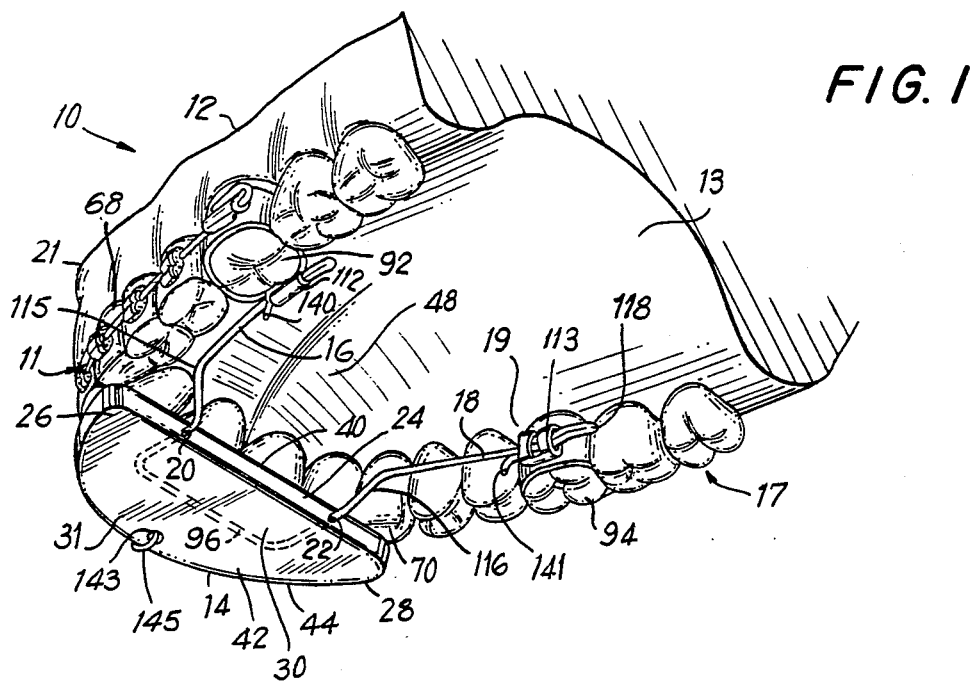
FIG. 1 is a perspective view of the device as mounted on the upper jaw.
Figure 2:
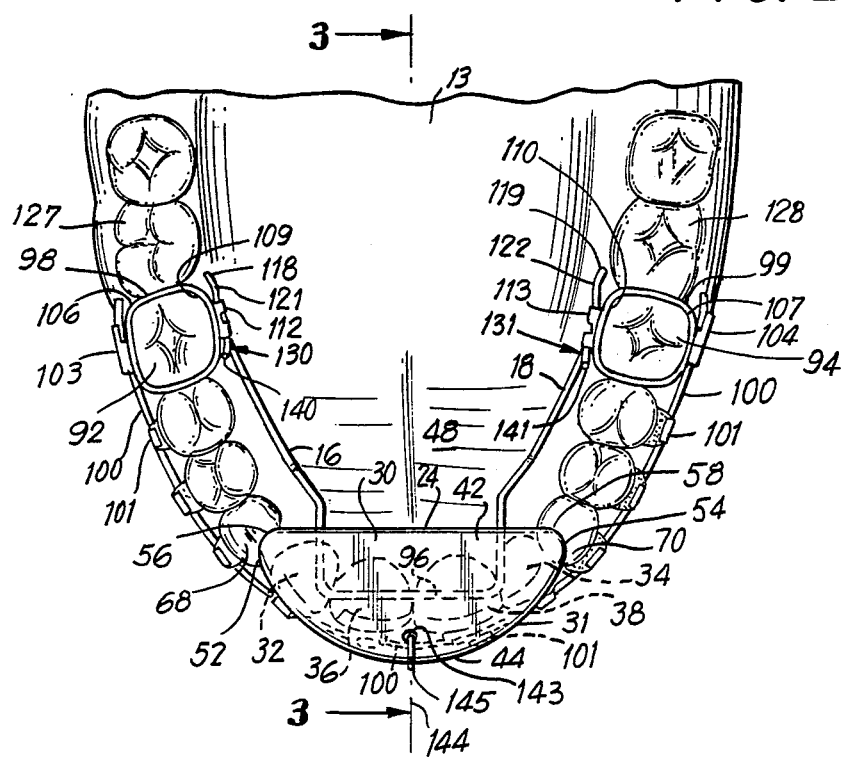
FIG. 2 is a top view of the device positioned under the anterior of the upper jaw.

FIG. 1 illustrates a perspective view of the device 10 according to the present invention. Device 10 is mounted under the upper anterior teeth 11 of the upper jaw 12 of mouth 13 of a patient. Device 10 includes a substantially flat plate 14 preferably of a resilient plastic and left and right side support wires 16 and 18 connected to plate 14 approximately at left and right midpoints 20 and 22 of rear wall 24 from where the side wires extend to selected upper posterior teeth of upper jaw 17, preferably left and right first molars 92 and 94 as illustrated in the drawings in a manner to be described. Wires 16 and 18 are preferably made of a pliable metal. Midpoints 20 and 22 are positioned in the left and right rear portions 26 and 28 of plate 14. As shown in FIG. 2, left and right side wires 16 and 18 are preferably joined together inside of rear portion 30 of plate 14, which is preferably made of a moldable thermoplastic material.

Figure 4:
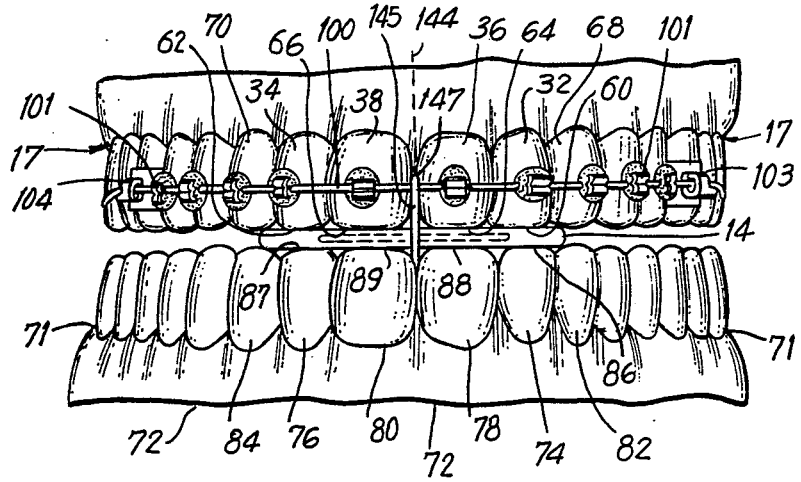
FIG. 4 is a front elevational view showing the device in position in relation to the anterior teeth of the upper and lower jaws.

As illustrated in FIGS. 1, 2, and 4, front portion 31 of plate 14 is positioned under the upper anterior teeth, which are set in inner or outer gingivae, or gums, 19 and 21, respectively. Plate 14 is set in particular under the lower edges of the central and lateral incisors of upper jaw 12, shown in FIG. 2 as left and right lateral incisors 36 and 38, respectively. Plate 14 in the preferred embodiment illustrated includes opposed top and bottom substantially parallel walls 40 and 42, respectively, which are spaced relatively closely. Top and bottom walls 40 and 42 intersect upright front wall 44, which is configured in a "C"-shaped upright wall configuration which follows the curved contour of the incisors of the upper dental arch of the anterior teeth of the upper jaw. Left and right bases 52 and 54 respectively of the "C" of the front wall 44 are intersected by upright rear wall 24, which extends substantially straight across the lower forward portion 48 of the mouth 13 in a plane positioned substantially perpendicular to the mesial of the jaw of the patient. Rear wall 24 and wall bases 52 and 54 are preferably joined by left and right upright curved wall portions 56 and 58 respectively. It is understood that plate 14 can be configured somewhat differently within the scope of the invention. For example, in place of rear wall 24 there could be a plane angled from top wall 40 meeting bottom wall 42 at an edge.

Figure 3:
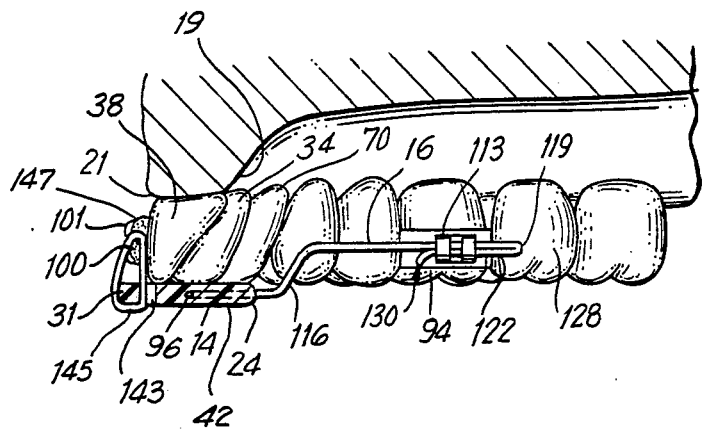
FIG. 3 is a sectional elevational view taken through line 2—2 of FIG. 2.

As shown in the front elevation of FIGS. 3 and 4, bottom wall 42 of plate 14 preferably is in touching contact with lower biting, or incisal, edges 60,62,64 and 66 of left and right lateral incisors and left and right central incisors 32,34,36, and 38, respectively. Because of the inherent unevenness of human teeth and because of the possibility one of the named incisors might be missing, it is not absolutely necessary for every incisal edge of every incisor be in touching contact with plate 14. Also, within the scope of the invention plate 14 could be constructed and arranged to be in touching contact with left and right central incisors 36 and 38 only, for example. In the preferred embodiment as illustrated, bottom wall 42 is in touching contact only with the incisor edges of the four upper incisors 32,34, 36, and 38, but is preferably disposed over a portion of left and right upper cuspids 68 and 69; when plate 14 is pressed upwards by the lower anterior teeth as shown in FIG. 4, plate 14 is adapted to come into partial contact with upper left and right cuspids 68 and 70 respectively. As illustrated in FIG. 4, when the patient's lower jaw 72 is brought up, the opposed lower anterior teeth, namely left and right lateral incisors 74 and 76 and left and right central incisors 78 and 80, respectively, having respective incisal edges 86,87,88, and 89, come into pressing contact with bottom wall 42 of plate 14, which in turn presses up into pressing contact with the incisal edges of mating upper incisors, at which time, in accordance with the present invention, the relative movement of upper and lower jaws 12 and 72 ceases, and lower posterior teeth 71(FIG. 4) are prevented from coming into occlusion with the upper posterior teeth 17. In the preferred embodiment, some upward pressure can be peripherally applied at a portion of left and right lower cuspids 82 and 84, respectively, which in turn would bring portions of bottom wall 42 into pressure contact with portions of left and right upper cuspids 68 and 70. This is possible in part because of the somewhat flexible, resilient aspects of thermoplastic plate 14. It is understood that this pressure is peripheral and that is it is not necessary within the scope of the invention.

Plate 14 is preferably anchored to the lower left and right upper first molars 92 and 94 by way of left and right side wires 16 and 18. The side wires are preferably connected to plate 14 approximately at vertical midpoints of rear wall 24 from which points they extend inwardly into plate 14, in which they are bonded during the molding process of plate 14, until, at a distance spaced from both rear and front walls 24 and 44 where they are joined to cross-wire portion 96, which extends across plate 14 approximately parallel with and spaced from rear wall 14, so that a single support wire is preferably used for the support wires 16 and 18.

The support wire includes side wires 16 and 18, which preferably are single strands and which extend past first molars 92 and 94. First molars 92 and 94 are provided with metal tooth jackets 98 and 99 respectively, which are fitted completely around the first molars in a known manner.

In the preferred embodiment by way of example braces are shown mounted in a known manner around the outside teeth of the upper dental arch from left first molar 92 to right first molar 94. The braces include brace wire 100 positioned at midheight on each of the upper teeth by brace mounts 101, which are connected to each of the affected teeth in a known manner at the mid-area of the outside faces of the teeth. Brace wire 100 is mounted at left and right first molars 92 and 94 at left and right outside sheaths 103 and 104 respectively, which in turn are connected to the outside walls 106 and 107 of first molars 92 and 94 respectively in a known manner. Similar inside sheaths are placed on inner, or lingual, walls 109 and 110 of first and second molars 92 and 94 respectively, which are opposed to outside walls 106 and 107 respectively. Left and right inner sheaths 112 and 113 are positioned at the inner walls 109 and 110 respectively of left and right first molars 98 and 99. Inner sheaths 112 and 113 are preferably "Universal" type molar sheaths known in the art, but of course, the invention could be applied to similar sheaths.

Single wires 16 and 18 fold back on themselves to make double strand portions 121 and 122, which extend back from ends 118 and 119 to a position immediately past inner sheaths 112 and 113 respectively, that is, between sheaths 112 and 113 and the upper anterior teeth and proximate to inner sheaths 112 and 113. Double strand portions 121 and 122 terminate at single strand ends 130 and 131 respectively, which in turn are bent downwardly to lock the wires to the sheath. Double strand portions are gripped by left and right sheaths 112 and 113 in a known manner. Folded end portions 118 and 119 of double strand portions 121 and 122 extend from inner sheaths 112 and 113 towards respective second molars 127 and 128. The distance of extension beyond the midpoint of the molars is preferably 5 to 7 millimeters. Double strand end portions 121 and 122 are bent inwardly, or lingually, at ends 118 and 119 as illustrated in FIG. 2, so as to form stops against horizontal outward sliding movement of double strand portions 121 and 122 towards the anterior teeth.

As shown in FIGS. 1,2, and 3, left and right side wires 16 and 18 have upward bends 115 and 116 respectively to reach a horizontal level sufficient to reach inner molar sheaths 112 and 113 without interference with the bicuspid or cuspid teeth. In addition, as shown in FIG. 2 in particular, side wires 16 and 18, simultaneously with respective downward and outward bends 115 and 116 follow the inner lower dental arch out of the way of the tongue. Wires 16 and 18, which are single strands, as stated, are folded back at distal end portions 118 and 119 respectively, which grip inner sheaths 112 and 113 respectfully. Contact between the tongue and folded end portions 118 and 119, which are disposed inwardly towards the tongue, will not produce interference with the tongue's movement because of the general location of the end portions and because of the general location of the end portions and because of the smooth shape of the folded ends.

Strand ends 130 and 131, which are proximate to inner sheaths 112 and 113 on the opposite side of the sheaths to folded end portions 118 and 119, are bent downwards and preferably slightly inwards to form left and right studs 140 and 141(FIG. 1) that act as stops against horizontal sliding movement of double strand portions 121 and 122 in sheaths 112 and 113 inwards away from the anterior teeth and consequent movement of plate 14 inwards. Thus plate 14 is locked into a relatively non-movable position against inward or outward horizontal movements by outwardly bent end portions 118 and 119 and by stop studs 140 and 141.

Plate 14 preferably forms a vertical aperture 143 in the center of front portion 31. Aperture 31 is positioned directly over the imaginary vertical middle 144 between left and right central incisors 36 and 38. A ligature 145 is preferably an 0.010 ss ligature tie, is disposed downwards through aperture 143, under bottom wall 40 up past front wall 44 to immediately above wire brace 100, which extends midway proximate to central incisors 36 and 38; here the ligature passes above brace wire 100 and downwards to aperture 143. The actual connecting tie 147 between the ends of the ligature is preferably accomplished near the outer gingiva 21. The ligature not only holds down plate 14 from vertical movement; it also accomplishes the task of making the removal of plate 14 and its replacement by the patient to be difficult, if not impossible, of accomplishment without having evidence of its removal and replacement made apparent to the orthodontist.

Figure 5:
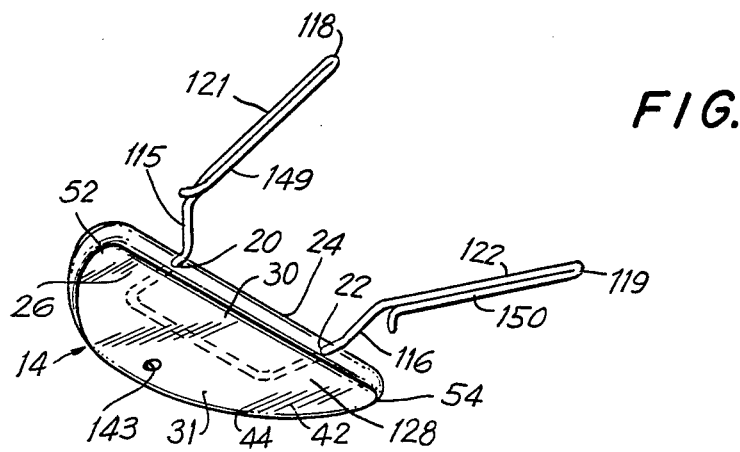
FIG. 5 is a perspective view of the device prior to being fitted to a patient by an orthodontist.

FIG. 5 illustrates device 10 including plate 14 and left and right side wires 16 and 18 prior to fitting to the patient by the orthodontist. In adjusting the device as shown in FIG. 5, the orthodontist first measures from the midline of the lower central incisors to 5 to 7 millimeters beyond the far edge of the sheaths of the anchor molars, preferably the first molars 92 and 94 as described above, and consequently beyond sheaths 112 and 113. Plate 14 is laid against the upper anterior incisors so that aperture 143 is positioned at midline 144 between the central incisors. Double strand portions 121 and 122 are bent inwards or outwards so that they rest on the inner sheaths. Next, the left and right return strands 149 and 150 are marked by appropriate means at the middle of sheaths 112 and 113 and thereupon turned upwards at the mark and preferably directed slightly inwards. The strands are then cut so as to leave the 2 to 3 millimeter stop studs 140 and 141 described above but not shown in FIG. 5, which shows over-extended return strands 149 and 150. Wires 16 and 18 are shaped and adapted so that they fit into the inner sheaths with ease and plastic plate 14 rests on the lower incisal edges as described. The doube strand portions 121 and 122 are then connected to their respective sheaths in a known manner. Folded end portions 118 and 119 are then bent inwards towards the tongue to form the stops described above. Finally, ligature 145 is set into position through aperture 143 and tied around wire brace 100 as described above so that ligature 145 further anchors plate 14 to the teeth of the lower jaw.

Figure 6:
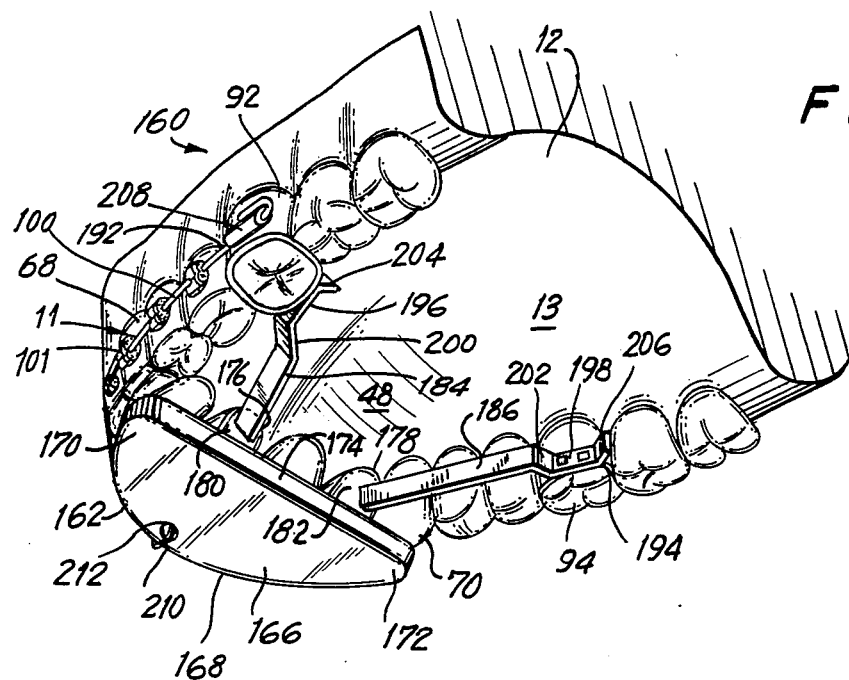
FIG. 6 is a perspective view of another embodiment of the present invention mounted on the upper jaw.
Figure 7:
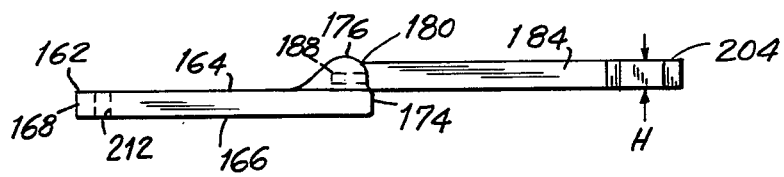
FIG. 7 is a side view in isolation of the invention shown in FIG. 6 showing the left side of the plate and a support wire.
Figure 8:
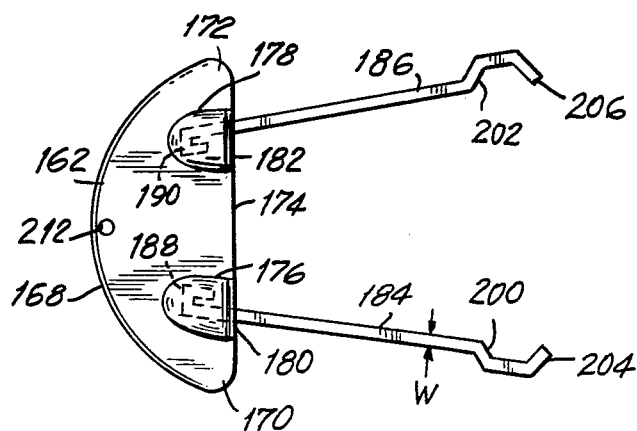
FIG. 8 is a top view of the device shown in FIG. 7.

A variation of device 10 as illustrated in FIG. 1 is shown in FIGS. 6, 7, and 8. FIG. 6 illustrates in perspective view an alternative embodiment of the present invention. As will be explained below in detail, the embodiment of FIG. 6 includes a pair of metal support wires of greater thickness and strength than wires 16 and 18 of the first embodiment, and also made of a pliable metal. In accordance with the present invention, a device designated as 160 is shown with left and right upper first molars 92 and 94. A substantially flat plate 162 of a moldable, preferably made of a resilient material such as plastic. Plate 162 is mounted under the upper anterior teeth 11 of the upper jaw 12 of a patient. Plate 162 has opposed substantially parallel upper and lower walls 164 and 166 respectively with a "C"-shaped upright front wall 168 which follows the curved contour of the incisors of the upper dental arch of the anterior teeth. Left and right bases 170 and 172 respectively of the front wall 168 are intersected by upright rear wall 174, which extends substantially straight across the forward portion 48 of mouth 13 in a plane positioned substantially perpendicular to the mesial of the jaw of the patient. The wall portions at bases 170 and 172 are preferably curved. Plate 162 is in touching contact with the lower biting, or incisal, edges of the left and right lateral incisors and the left and right central incisors (not shown in FIG. 6) in the same manner as plate 14 of device 10. Again, like plate 14, plate 162 is adapted to come into partial contact with upper left and right cuspids 68 and 70.

As best seen in FIGS. 7 and 8, plate 162 also includes a pair of raised left and right posts 176 and 178 positioned on upper wall 164 proximate to rear wall 174. Posts 176 and 178 have substantially vertical rear walls 180 and 182 respectively that are proximate to vertical rear wall 174 of plate 14. As seen in the top view of FIG. 8, posts 176 and 178 are spaced inwards from bases 170 and 172 at a distance calculated to accomodate left and right support wires 184 and 186 respectively at an advantageous position to avoid interference with the patient's tongue and at the same time to avoid contact with the roof of the patient's mouth. Posts 176 and 178 are, as shown in FIG. 7, raised from the surface of upper wall 164 also a sufficient distance to accomodate the embedded ends 188 and 190 of wires 180 and 182 respectively. Also, embedded ends 184 and 186 extend into the posts, which must in turn extend away from rear wall 174 sufficiently to accommodate the ends. Since ends 184 and 186 are, as shown in FIG. 8, preferably configured in left and right horizontal hook configuration so as to secure the wires to the posts. The posts are also of sufficient width to accommodate the described hoods. The configuration of posts 176 and 178 are preferably oval shaped so as to reduce catching on the roof of the patient's mouth. Posts 176 and 178 are preferably molded integral with plate 162, which, like plate 14, is preferably of thermoplastic material.

Extending from posts 176 and 178 are, as stated, wires 184 and 186. It is to be noted that wires 184 and 186 are much heavier and stronger that wires 16 and 18 of device 10, and it is for this reason that plate 162 takes on a different configuration than plate 14. But device 160 differs in other ways from device 10 in that wires 184 and 186 also are configured somewhat differently than wires 16 and 18. Wires 184 and 186 extend straight from posts 176 and 178 at a slight angle towards left and right first molars 92 and 94 respectively. Wires 184 and 186 are preferably of the approximate dimensions of between 0.033 to 0.034 mm in width W and 0.065 mm in height H. Designations W and H are indicated in FIGS. 6 and 7 respectively. As noted previously, wires 184 and 186 approach first molars 92 and 94 at a slight angle moving from an inward position to an outward position. First molars 92 and 94 are provided with metal jackets 192 and 194 respectively with lingual sheaths 196 and 198 respectively. Lingual sheaths 196 and 198 are preferably approximately 0.036 mm. Wires 184 and 186 each have outward bends 200 and 202 respectively. Bends 200 and 202 are preferably no greater than 45 degrees. Bends 200 and 202 are disposed adjacent to respective sheaths 196 and 198 to which wires 184 and 186 are respectively joined. Bends 200 and 202 because of their placement in relation to the lingual sheaths act as stops that prevent inward sliding movement of the wires within the sheaths and consequent inward shifting of plate 162. After the 45 degree bends 200 and 202, wires 184 and 186 are connected to upper first molars 92 and 94 at sheaths 196 and 198. Wires 184 and 186 immediately upon emerging from the sheath connections are bent outwardly at respectively flange ends 204 and 206, which act as retainers to prevent outward sliding of the wires within the sheaths.

Stop bends 200 and 202 perform the same function as left and right strand ends 130 and 131 for wires 16 and 18 of device 10 of the prior embodiment, that is, prevent inward sliding movement of the wires in the sheaths. Likewise, flange ends 204 and 206 perform the same function as left and right double strand ends 118 and 119, which are bent, so that the support wires do not slide outwards in the sheaths.

FIG. 6 also shows brace wire 100 with brace mounts 101 on the outside of the upper teeth and attached to left outer sheath 208 on first molar 92. The right outer sheath cannot be seen in FIG. 6. A ligature 208 passes through central front aperture 212 tying plate 162 to wire 100 in the same manner as ligature 145 ties plate 14 to braces wire 100 in the first embodiment.

Various departures from the exact embodiments just described also fall within the scope of the invention. For example, a ligature tie could be made at left and right stop studs 140 and 141 to fasten left and right side wires 16 and 18 to wire brace 100. Also, it is noted that the position of a tooth on the jaw is not static. The presence of irregular teeth, supernumerary teeth, tilted teeth, misaligned teeth, missing teeth, and malocclusions between teeth that would make it necessary to adapt the device as described would not in itself affect the spirit of the invention as here set forth. Other embodiments can be made. For example, the wire connectors may be adjusted in size and configuration within the spirit of the invention.

The embodiments of the invention particularly described here are presented merely as examples of the invention. Other embodiments, forms, and modifications of the invention coming from the proper scope of the appended claims will, of course, readily suggest themselves to those skilled in the art.

What is claimed is:

1. An orthodontic device, comprising in combination:
   plate means mounted over selected upper anterior teeth for preventing contact between said upper anterior teeth and the opposed lower anterior teeth, and
   wire means connected to said plate means and to selected upper posterior teeth for anchoring said plate means to said upper posterior teeth, said selected upper anterior teeth including lateral and central incisors, said selected upper posterior teeth including the first molars, said plate means including substantially parallel top and bottom walls intersected by a vertical rear wall that extends substantially at right angles to the mesial of the mouth and a generally C-shaped front wall configured in accordance with said upper anterior incisors, said wire means including a pair of strands each having one end connected to said plate at said rear wall and the other end being folded back into a double strand position including a folded distal end and a strand end positioned between said folded end and said plate, said orthodontic device further including jackets mounted around each of said upper first molars and sheaths connected to the inner walls of said jackets, each said double strand portion being slidably mounted to said sheaths, said sheaths being disposed between said folded distal ends and said strand ends, said folded distal ends being bent inwardly and said strand ends are bent upwardly, whereby said folded distal ends and said strand ends form stops adapted to prevent said double strand portions from sliding in said sheaths, whereby said plate is prevented from sliding, said folded distal portions extending approximately 5 to 7 millimeters past said sheaths and said strand ends extending approximately 2 to 3 millimeters upward, said pair of strands having down bends between said rear wall of said plate to the level of said sheaths, said down bends being closely spread to said rear wall, said pair of strands extending outwardly from said plate spaced from the inner wall of the upper cuspid teeth to said sheaths, said pair of strands being disposed within and bonded to said plate and further being joined in said plate to form a single strand.

2. An orthodontic device according to claim 1, said plate forming a centrally disposed vertical aperture closely spaced from said front wall, said aperture being positioned over the center line of the lower central incisors, the upper teeth being provided with a brace wire mounted to the front walls of said upper teeth, and a ligature means positioned through said aperture and under said brace wire for further anchoring said plate to said lower teeth.

3. An orthodontic device according to claim 2, wherein said plate is made of a thermoplastic material.

4. An orthodontic device according to claim 3, wherein said pair of strands are made of a pliable metal.

5. An orthodontic device according to claim 1, further including a pair of posts disposed on said top wall adjacent to said rear wall.

6. An orthodontic device according to claim 5, wherein said wire means includes a pair of wires each having one end portion connected to each of said posts and having end portions.

7. An orthodontic device according to claim 6 further including jackets mounted around each of said upper first molars and sheaths connected to the inner walls of said jackets, each of said end portions being slidably mounted to each of said sheaths.

8. An orthodontic device according to claim 7, wherein each of said wires includes a stop bend adjacent to each of said sheaths on the anterior side and a flange retainer adjacent to each of said sheaths on the posterior side, whereby said sires are prevented from sliding in said sheaths.

9. An orthodontic device according to claim 8, wherein said wires have a height dimension and a width dimension, said height dimension being approximately 0.034 mm and said width dimension being approximately 0.065 mm.

* * * * *